United States Patent

Breukelaar et al.

[11] Patent Number: 5,089,458
[45] Date of Patent: Feb. 18, 1992

[54] SYNTHETIC SAPONITE-DERIVATIVES, A METHOD FOR PREPARING SUCH SAPONITES AND THEIR USE IN CATALYTIC (HYDRO) CONVERSIONS

[75] Inventors: Johan Breukelaar; Rutger A. Van Santen; Andreas W. De Winter, all of Amsterdam, Netherlands

[73] Assignee: Shell Oil Company, Houston, Tex.

[21] Appl. No.: 520,484

[22] Filed: May 7, 1990

[30] Foreign Application Priority Data

May 19, 1989 [GB] United Kingdom ................ 8911610

[51] Int. Cl.$^5$ .............................................. B01J 21/16
[52] U.S. Cl. ........................................ 502/63; 502/80; 502/84
[58] Field of Search ............................ 502/84, 63, 80

[56] References Cited

U.S. PATENT DOCUMENTS

| | | | |
|---|---|---|---|
| 3,844,979 | 10/1974 | Hickson | 502/84 |
| 3,852,405 | 12/1974 | Granquist | 423/118 |
| 3,959,118 | 5/1976 | Granquist | 208/120 |
| 4,666,877 | 5/1987 | Vaughan | 502/84 |

Primary Examiner—Carl F. Dees

[57] ABSTRACT

The invention relates to saponite-derivatives according to the general formula $$A_{x/n}{}^{n+} [(Mg_{3-y}M_y)(Si_{4-x}Al_x)O_{10}(OH_{2-z})F_z]$$

wherein A represents an (alkyl-substituted) ammonium ion and/or any metal having basic or amphoteric properties, M represents a bivalent metal ion having an ionic radius between 0.050 and 0.085 nm, n represents the valence of A, x represents a number between 0.05 and 1.5, y represents a number between 0.05 and 2.95 and z represent a number from 0 to 1.8. The invention also relates to methods for preparing such saponite-derivatives, catalytically active system based on such saponite-derivatives and their use in various hydrocarbon conversion processes.

27 Claims, No Drawings

SYNTHETIC SAPONITE-DERIVATIVES, A METHOD FOR PREPARING SUCH SAPONITES AND THEIR USE IN CATALYTIC (HYDRO) CONVERSIONS

FIELD OF THE INVENTION

The present invention relates to synthetic saponites, a method for preparing such saponites and their use in catalytic (hydro)conversion processes.

BACKGROUND OF THE INVENTION

There is considerable interest in so-called swellable clays which can be used, interalia, in the preparation of pillared clays which are considered promising alternatives to zeolites, in particular since larger pores can be obtained than available with zeolites, provided a proper choice of pillaring materials has been made.

Saponites belong to the family of smectic clays, i.e. swellable compounds, which also include montmorillonites, hectorites, nontronites and beidellites. Both flurine-containing and fluorine-free saponites are known.

An interesting structural feature concerning saponites, normally represented by the formula

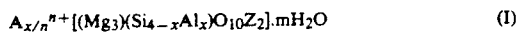
$$A_{x/n}{}^{n+}[(Mg_3)(Si_{4-x}Al_x)O_{10}Z_2] \cdot mH_2O \qquad (I)$$

wherein A usually represents lithium, sodium or calcium, x represents a value between 0.05 and 0.95, n represents the valence of A, Z represents a fluorine and/or a hydoxyl group and m has typically a value between 2 and 5, is that magnesium is situated in the octahedral layer at the centre of the triple layer sheet of the smectic clay.

A novel class of saponite-derivaties has now been found which have interesting propertise both as catalyst carriers and under certain conditions as catalysts themselves. The saponite-derivatives according to the present invention can moverover also be prepared under rather mild process conditions which widely enlarges their applicability.

SUMMARY OF THE INVENTION

The present invention relates to novel saponite-derivatives according to the formula

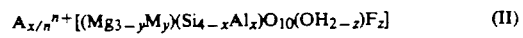
$$A_{x/n}{}^{n+}[(Mg_{3-y}M_y)(Si_{4-x}Al_x)O_{10}(OH_{2-z})F_z] \qquad (II)$$

wherein A represents an (alkyl-substituted) ammonium ion and/or any metal having basic or amphoteric properties, M represents a bivalent metal ion having an ionic radius between 0.050 and 0.085 nm, n represents the valence of A, x represents a number between 0.05 and 1.5, y represents a number between 0.05 and 2.95 and z represents a number from 0 to 1.8.

DETAILED DESCRIPTION OF THE INVENTION

Suitably, A represents a lithium, sodium, potassium, calcium or ammonium ion. Examples of compounds capable of providing the moiety A are ammonium hydroxide, ammonium acetate, sodium hydroxide, potassium hydroxide and calcium hydroxide. Preferably, A represents an ammonium ion.

Examples of suitable bivalent metal ions having ionic radii between 0.050 and 0.085 comprise iron, nickel, cobalt, mangnese, copper and zinc as well as mixtures thereof. Preferred bivalent metal ions are nickel and cobalt.

Suitably, the value for y ranges between 0.05 and 2.5. A preferred range for y is between 0.5 and 2.5. The value for x suitably ranges between 0.20 and 1.25. The value for z suitably ranges from 0 to 1.25.

The saponite-derivatives according to the present invention can be suitably prepared by reacting under hydrothermal conditions a silicon source, an aluminium source, a magnesium source, a source of (alkyl-substituted) ammonium ions and/or any metal ion having basic or amphoteris properties, a fluoride source when z represents a number $>0$ and optionally a further source containing M metal ions.

Preferably, the saponite-derivatives according to the present invention can be prepared by maintaining a silicon source, an aluminium source, a magnesium source, a source of (alkyl-substituted) ammonium ions and/or any metal ion having basic or amphoteric properties, a fluoride source when z represents a number $>0$ and optionally a furthe source containing M metal ions under aqueous conditions at a temperature between 125° and 280° C. for a period of time sufficient to form said saponite-derived.

Most preferably, the saponite-derivatives according to the rpesent invention can be prepared by maintainnig the appropriate sources under aqueous conditions at a temperature between 145° and 250° C., in particular between 150° and 200° C.

It should be noted that saponite-type mineral compositions, preferably containing an accessory phase of (MgO,OH) are known to be prepared at a temeprature of 300° C. (U.S. Pat. No. 3,959,118).

It is described in U.S. Pat. No. 3,852,405 that laminar 2:1 layer lattice aluminosilicate minerals can be prepared by maintianing an aqueous mixture of the appropriate starting materials at a temperature between 280° and 310° C.

The process according to the present invention is suitably carried out in such a way that the pH of the aqueous solution initially ranges between 6.5 and 10. The process according to the present invention is suitably carried out under such conditions that the aqueous solution finally reaches a lower pH value in the range between 3 and 8.5.

This can be suitably achieved by selecting the proper conditions, in particular the source of magnesium, in the starting mixture.

Suitable magnesium sources comprise inorganic magnesium salts such as magnesium nitrate, magnesium sulphate and magnesium halides as well as magnesium salts of organic acids such as magnesium formate, magnesium acetate and magnesium propionate. Also magnesium hydroxide can be used as a source of magnesium. Preference is given to the use of magnesium nitrate or magnesium acetate as source of magnesium.

As silicon source(s) for the process according to the present invention an suitably be used amorphous silica as well as organic silicon compounds such as silicon esters and silanes which can be converted to siica by methods known in the art. If desired, the silicon source can be subjected to a heat treatment prior to its use in the process according to the present invention.

Suitable aluminium souces comprise aluminas such as alpha, gamma or eta-alumina as well as various boehmite forms which can be converted into alumina by methods known in the art. Also organic aliuminium compounds such as aluminium alkoxides and Al salts or organic acids, in particular aluminium tri-isopropylate can suitably be used in the process according to the present invention.

Further, the aluminium source can be subjected to a heat treatment prior to its use in the process according to the present invention. Also amorphous silica-alumina as well as crystalline (alumino)silicates can be used as silica and/or alumina source in the process according to the present invention.

It should be noted that the silicon source and the aluminium source should be used normally in such an amount that a molar sum (Si+Al) of 4 will be achieved in the general formula II whilst ascertaining at the same time that the molar ratio $SiO_2/Al_2O_3$ is between 3.33 and 160. Preferably the molar ratio is below 80. Good results have been obtained using a silica/alumina molar ratio between 4.5 and 40.

The present invention also relates to catalytically active systems based on a saponite-derivative according to the general formula II and a furtehr catalytically active material. Suitably, one or more metals and/or metal compounds according to Group VI and/or VIII of the Periodic Table of the Elements are present in the catalystically active system based on a saponite-derivative as described hereinabove.

Preference is given to the presence of one or more metal(s) or metal compound(s) of nickel, cobalt, molybedenum, tungsten, platinum or palladium in the catalytically active systems in accordance with the present invention.

Suitably the catalytically active systems in accordance with the present invention also contain alumina, silica, silica-alumina or a crystalline (metallo)silicate.

It is possible to introduce the metal(s) or metal compound(s) according to Group VI and/or VIII into the saponite-derivative based catalytic systems via alumina, silica, silica-alumina or a crystalline (metallo)silicate.

The present invention further relates to the use of saponite-derivatives as base materials for certain (hydro)conversion processes as well as in oligomerization processes.

When saponite-derivatives in accordance with the presen tinvention are used in a process directed at hydrocracking of hydrocarbonaceous materials they are preferably saponite-derivatives wherein M represents a Ni moiety. The saponite-derivative-based catalyst systems for use in hydrocracking are preferably those wherein A represents a H+ moiety. Such system can be either obtained by (thermal) decomposition of as-synthesised forms wherein A represents an (alkyl-substituted) ammonium ion or by ion exchange or impregnation techniques when A represents said (alkyl-substituted) ammonium ion or any other ion as defined hereinbefore.

As catlytically active materials can suitably be used platinum and/or palladium or nickel and/or tungsten. When use is made of platinum and/or palladium as catalytically active material(s) it is preferred to subject the saponite-derivative based system containing a platinum and/or a palladium compound to ar educing treatment in order to acquire the envisaged catalytic activity. When use is made of nickel and/or tungsten compounds as catalytically active materials is is preferred to subject the saponite-derivative to a reducing treatment prior to the incorporation of the metal compound(s) into the saponite-derivative.

Reducing treatments can be carried out conveniently by methods known in the art, e.g. a treatment with a hydrogen containing gas at elevated temperature.

Prior to or following the reducing treatment the (catalytically active) system obtained may be subjected to a heat treatment. Such heat treatment, e.g. a calcination treatment can be suitably carried out at a temperature between 300° and 800° C., preferably between 400° and 600° C.

The hydrocracking process wherein catalysts are used based on saponite-derivatives according to the general formula II is suitably carried out at a temperature in the range between 250° and 450° C. and at a pressure between 30 and 175 bar. Preferably, the hydrocracking is carried out at a temperature in the range between 300° and 425° C. and at a pressure in the range between 50 and 150 bar.

When sapponite-derivatives in accordance with the present invention are used in a process directed at hydroisomerisation of hydrocarbonaceous materials they are preferably saponite-derivatives wherein M represents nickel and which in their reactive forms have A representing H+ and which also contain platinum and/or palladium which may have been introduced via an alumina carrier. Systems wherein A represents a H+ moiety can be obtained by the same methods as described hereinbefore for the catalysts to be used in hydrocracking.

It is preferred to use catalysts based on saponite-derivatives in hydroisomerisation processes after they have been subjected to a reducing treatment. Reducing treatments can be carried out conveniently by methods known in the art, e.g. a treatment with a hydrogen containing gas at elevated temperature. Prior to or following the reducing treatment the (catalytically active) system obtained may be subjected to a heat treatment. Such heat treatment, e.g. a calcination treatment can suitably be carried out at a temperature between 30° and 800° C., preferably between 400° and 600° C.

Hydroisomerisation processes wherein catalysts are applied based on saponite-derivatives according to the general formula II are suitably carried out at a total pressure in the range of form 1 to 70 bar and at a temperature in the range of from 150° to 350° C. Preferably, the hydroisomerization processes are carried out at a total pressure in the range of from 5 to 50 bar and at a temperature in the range of form 175° to 275° C.

The hydrocarbonaceous materials to be hydroisomerised suitably comprise alkanes, in particular alkanes having up to 10 carbon atoms. Preferably, feedstocks containing alkanes having 4 to 7 carbon atoms are subjected to the hydroisomerisation in accordance with the present invention. Good results have been obtained using n-hexane as feedstocks.

When saponite-derivatives in accordance with the present invention are to be used in a process directed at the oligomerization of hydrocarbonaceous materials they are preferably saponite-derivatives wherein A represents a H+ moiety and which also contain a metal compound of one or more of nickel, cobalt, palladium or chromium. Systems wherein A represents a H+ moiety can be obtained by the same methods as described hereinabove for the catalysts to be used in hydrocracking and/or hydroisomerization.

Suitably, use is made of catalysts based on saponite-derivatives according to the general formula II which have been subjected to a reducing treatment. The reducing treatment can be carried out conveniently by methods known in the art, e.g. a treatment with a hydrogen containing gas at elevated temperature. It should be noted that no such treatment is needed when ethylene is used as feedstock. Prior to or following the reducing treatment the (catalytically active) system obtained may be subjected to a heat treatment. Such heat treatment can be suitably carried out at a temeprature in the range between 300° and 800° C., preferably between 400° and 600° C.

Oligomerization processes wherein use is made of catalysts based on saponite-derivatives according to the general formula II are suitably carried out at a temperature in the range between 80° and 250° C. and at a pressure in the range between 10 and 100 bar. Preferably, oligomerization processes in accordance with the present invention are carried out at a temperature in the range between 110° and 225° C. and at a pressure in the range between 30 and 80 bar.

Feedstocks which can be suitably applied in the oligomerization processes according to the present invention comprise hydocarbonaceous materials containing one or more alkenes having up to 14 carbon atoms. Preferably, feedstocks having of from 2 to 6 carbon atoms are subjected to oligomerization in accordance with the present invention.

In particular, the catalysts based on saponite-derivatives according to the general formula II can be used in the oligoemrization of ethylene containing feedstocks. Suitable ethylene sources comprise feedstocks which produce ethylene by steam cracking of hydrocarcker bottoms obtained in refinery operations. Preferred catalysts systems are those wherein A represents an (alkyl-substituted) ammonium ion and/or any metal ion having basic or amphoteric properties and wherein as bivalent metal ion nickel is used.

It will be clear that the effluents from the various (hydro)conversion processes can be subjected to further upgrading steps, if necessary, which steps are known to those skilled in the art such as, for instance, separation using molecualr sieves, distillation and hydrogenation treatments.

The ranges and limitations provided in the instant specification and claims are those which are believed to particularly point out and distinctly claim the instant invention. It is, however, understood that other ranges and limitations that perform substantially the same function in substantially he same way to obtian the same or substantially the same result are intended to be within the scope of the instant invention as defined by the instant specification and claims.

The invention will be described by the following examples which are provided for illustration purposes and are not to be construed as limiting the invention.

EXAMPLE 1

40 grammes of amorphous silica-alumina (containing 13 wt % alumina) was thoroughly mixed with 36.5 grammes of (Mg(OAc)$_2$.4H$_2$O and 84.7 grammes of Ni(OAC)$_2$.4H$_2$O. This mixture having a molar composition $$SiO_2:Al_2O_3:MgO:NiO = 3.40:0.30:1.00:2.00$$

was subsequentialy added to 75.4 grammes of water to which 13.9 grammes of a solution of 25 wt % ammonia was added, under stirring. This suspension was then transferred to an autoclave.

The temperature was raised to 240° C. and maintained at that temperature for a period of 60 hours. Thereafter the autoclave was cooled to room temperature and the contents of the autoclave were dispersed in a vessel containing four liters of water. The mixture was sedimented and washed several times with water, after which the synthetic saponite-derivative obtained was additionally treated with a NH$_4$Cl solution. Nickel saponite was obtained in an amount of 46.0 grammes.

EXAMPLE 2

The experiment as described in Example 1 was repeated but using 73.1 grammes of Mg(OAc)$_2$.4H$_2$O and 42.3 grammes of Ni(OAc)$_2$.4H$_2$O to produce a mixture having a molar composition $$SiO_2:Al_2O_3:MgO:NiO = 3.40:0.30:2.00:1.00$$

45. 2 grammes of nickel saponite were obtained.

EXAMPLE 3

The experiment as described in Example 1 was repeated whilst maintaining a temperature of 190° C. for a period of 120 hours. 43.0 grammes of nickel saponite were obtained.

EXAMPLE 4

A nickel saponite as described in Example 1 was calcined at 550° C. and used in the oligomerization of ethylene. A feedstock of ethylene and helium (molar ratio ethylene/helium 2) was passed over the calcined nickel saponite at a weight hourly space velocity of 4.4 g/g/h at a temperature of 180° C. and a total pressure of 30 bar.

After 20 hours of operation the conversion, expressed as (ethylene, in - ethylene,out)/ethylene,in, amounted to 54%. The selectivity to oligomers (up to C$_{10}$) amounted to 9.5%.

EXAMPLE 5

The experiment described in the previous Example was repeated using a nickel saponite as described in Example 2 which had been subjected to a calcination treatment at 550° C. and using a butane/butene feedstock containing 51.6 wt % n-butane, 9.9 wt % i-butane, 19.2 wt % butene-1 and 19.2 wt % butene-2. The oligomerization was carried out at a temperature of 214.5° C., a butane/butene pressure of 14.9 bar and a weight hourly space velocity of 2.5 g/g/h.

After 20 hours of operation he butenes converstion amount to 68.7%.

EXAMPLE 6

An experiment was carried out to measure the isomerisation of n-hexane. A nickel saponite as described in Example 1 was used after calcination at 550° C. followed by an ion-exchange treatment to load the nickel saponite with platnium and palladium to 0.3 and 0.5 wt %. respectively, calculated on total composition after a treatment with hydrogen at 360° C. for a period of 10 hours.

The isomerisation was carried out using a hydrogen/n-hexane feedstock having a molar ratio of 4 and at a temperature of 260° C., a hydrogen partial pressure of 30 bar and a weight hourly space velcotity of 2 g/g/h.

After 20 hours of operation the conversion of n-hexane, expressed as (n-hexane,in - n-hexane,out)/n-hexane,in, amounted to 77 wt % and the selectivity to C6-isomers was found to be 96%.

EXAMPLE 7

The experiment as described in the previous Example was repeated using a nickel saponite as described in Example 3 which had been subjected to a calcination treatment at 550° C. after which it was mixed with platinum on gamma-alumina (1.0 wt % Pt on total composite) and subjected to a treatment with hydrogen at 350° C. for a period of 10 hours.

The isomerisation treatment was carried out at 250° C. using a hydrogen/n-hexane feedstock having a molar ratio of 30. The hydrogen partial pressure amounted to 30 bar and the isomerisation was carried out at a weight hourly space velocity of 2 g/g/h.

After 5 hours of operation the conversion, expressed as (n-hexane,in - n-hexane,out)/n-hexane,in, amounted to 18.8 wt % and the selectivity to C6-isomers was found to be 78%.

We claim:

1. A saponite-derivative according to the general formula

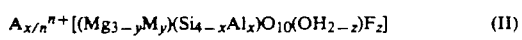
(II)

wherein A represents an (alkyl-substituted) ammonium ion and/or any metal having basic or amphoteric properties, M represents a bivalent metal ion having an ionic radius between 0.050 and 0.085 nm, n represents the valence of A, x represents a number between 0.05 and 1.5, y represents a number between 0.05 and 2.95 and z represents a number from 0 to 1.8.

2. The saponite-derivative according to claim 1 wherein z ranges from 0 to 1.25 and A, M, n, x and y are as defined hereinabove.

3. The saponite-derivative according to claim 1 wherein A represents a lithium, sodium, potassium, calcium or ammonium ion.

4. The saponite-derivative according to claim 3 wherein A represents an ammonium ion.

5. The saponite-derivative according to claim 1 wherein M represents one or more of iron, nickel, cobalt, manganese, copper or zinc ions.

6. The saponite-derivative according to claim 5 wherein M represents nickel and/or cobalt ions.

7. The saponite-derivative according to claim 1 wherein y ranges between 0.05 and 2.5.

8. The saponite-derivative according to claim 7 where y ranges between 0.5 and 2.5.

9. The saponite-derivative according to claim 1 wherein x ranges between 0.20 and 1.25.

10. The saponite-derivative according to claim 1 wherein A represent ammonium ion, M represents nickel and/or cobalt ions, y ranges between 0.5 and 2.5 and x ranges between 0.20 and 1.25.

11. The saponite-derivative according to the general formula

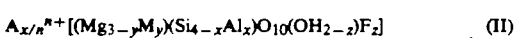
(II)

wherein A represents an (alkyl-substituted) ammonium ion M represents one or more iron, nickel, cobalt, manganese, copper or zinc, n represents the valence of A, x represents a number between 0.20 and 1.25, y represents a number between 0.5 and 2.5 and z represents a number from 0 to 1.8.

12. The saponite-derivative of claim 11 wherein A represents an ammonium ion and M represents nickel and/or cobalt.

13. A process for preparing the saponite-derivative according to claim 1 which comprises reacting under hydrothermal conditions a silicon source, an aluminium source, a magnesium source, a source of (alkyl-substituted) ammonium ions and/or any metal having basic or amphoteric properties, a fluoride source when z represents a number >0 and a further source containing M metal ions.

14. The process according to cliam 13 which omrpsies maintaining a silicon source, an aluminum source, a magnesium source, a source of (alkyl-substituted) ammonium ions and/or any metal ion having basic or amphoteric properties, a fluoride source when z represents a number >0 and a further source containing M metal ions under aqueous conditions at a temperature between 125° and 280° C. for a time sufficient to form said saponite-derivatives.

15. The process according to claim 14 wherein the appropriate sources are maintained under aqueous conditions at a temperature between 145° and 250° C.

16. The process according to claim 15 wherein the appropriate sources are maintained under aqueous conditions at a temperature between 180° C. and 250° C.

17. The process according to any one of claims 13-16 which is carried out in such a way that the pH of the aqueous solution initially ranges between 6.5 and 10.

18. The process according to any one of claims 13-16 which is carried out in such a way that the aqueous solution finally reaches a lower pH in the range between 3 and 8.5.

19. The process according to claim 13 which comprises using amorphous silica or an organic silicon compound as silicon source.

20. The process according to claim 13 which comprises using alpha-alumina, gamma-alumina, eta-alumina, a boehmite or an aluminium alkoxide or an Al salt of an organic acid as aluminium source.

21. The process according to claim 13 which comprises using the silicon source and the aluminium source in such an amount that a molar sum (Si+Al) of 4 will be achieved in the saponite-derivative according to formula II whilst ascertaining at the same time that the molar ratio $SiO_2/Al_2O_3$ is between 3.33 and 160.

22. The process according to claim 21 wherein use is made of a $SiO_2/Al_2O_3$ molar ratio below 80.

23. The process according to claim 22 wherein use is made of a $SiO_2/Al_2O_3$ molar ratio between 4.5 and 40.

24. A catalytically active system based on a saponite-derivative according to claim 1 containing one or mroe metals and/or metal compounds according to Group VI and/or Group VIII of the Periodic Table of the Elements.

25. The catalytically active system according to claim 24 wherein one or more metals or metal compounds of nickel, cobalt, molybdenum, tungsten, platinum or palladium are present in the system.

26. The catalytically active system according to claim 24 or 25 which additionally contains alumina, silica, silica-alumina or a crystalline (metallo)silicate.

27. A process for preparing a catalytically active system according to claim 24 by introducing the metal(s) and/or metal compound(s) according to Group VI and/or VIII into the material via alumina, silica, silica-alumina or a crystalline (metallo)silicate.

* * * * *